United States Patent
Tu et al.

[19]

[11] Patent Number: 6,017,324
[45] Date of Patent: Jan. 25, 2000

[54] DILATATION CATHETER HAVING A BIFURCATED BALLOON

[76] Inventors: Lily Chen Tu; Hosheng Tu, both of 2151 Palermo, Tustin, Calif. 92782

[21] Appl. No.: 09/175,714

[22] Filed: Oct. 20, 1998

[51] Int. Cl.[7] .................................................. A61M 29/00
[52] U.S. Cl. .................................... 604/96; 604/5; 604/9
[58] Field of Search ............................ 604/98–102, 500, 604/508, 509; 606/192, 194, 108; 623/1, 112

[56] References Cited

U.S. PATENT DOCUMENTS

| | | | |
|---|---|---|---|
| 5,320,604 | 6/1994 | Walker et al. | 604/96 |
| 5,470,313 | 11/1995 | Crocker et al. | 604/96 |
| 5,591,228 | 1/1997 | Edoga | 623/1 |
| 5,613,980 | 3/1997 | Chauhan | 606/194 |
| 5,669,924 | 9/1997 | Shanknovich | 606/108 |
| 5,720,735 | 2/1998 | Dorros | 604/284 |

OTHER PUBLICATIONS

Gabriel Spera "The Next Wave in Minimally Invasive Surgery" MD&DI pp. 36–44, Aug. 1998.

*Primary Examiner*—Wynn Wood Coggins
*Assistant Examiner*—Deborah Blyveis

[57] ABSTRACT

A dilatation catheter includes an inflation balloon having a bifurcated inflation profile at its distal portion. The balloon is securably attached on a guidewire, wherein the guidewire has a two-head distal region with two guidewire distal ends, a first guidewire distal end being capable of advancing into a first vessel while a second guidewire distal end being capable of advancing into a second branch vessel. The bifurcated balloon is to be inflated so that the diameters of the two stenotic vessels at the bifurcation region are enlarged simultaneously. In an alternate embodiment, a dilatation catheter comprising an inflatable bifurcated balloon, wherein a deployable bifurcated stent is wrapped around and on the bifurcated balloon of a dilatation catheter.

1 Claim, 6 Drawing Sheets

DILATATION CATHETER HAVING A BIFURCATED BALLOON

The present invention generally relates to catheters for insertion into a body lumen. More particularly, the present invention relates to a stent delivery and balloon dilatation catheter for use in the vascular system, wherein the catheter has a bifurcated balloon to treat the tissues at a bifurcated region of the vascular system.

BACKGROUND OF THE INVENTION

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. A wide variety of catheters have been developed in the prior art for percutaneous transluminal coronary or peripheral vascular applications. One example is a balloon dilatation catheter for performing percutaneous transluminal coronary angioplasty, which is well known in the art.

An artery is one of the tube-shaped blood vessels that carry blood away from a heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Accumulation of fatty substances occurs most often at the site of bifurcated branches where the separation of flows favors the deposition of fatty substances. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

There are limitations, however, to this technique's application, depending on the extent of the disease, the blood flow through the artery, and the part of the anatomy and the particular vessels involved. Prior art vascular dilatation balloons are axially straight and are most effective in a relatively straight vessel. However, plaque build-up and/or severe stenosis mostly occur at the point of vessel bifurcation where the blood flow is turbulent and the deposition of fatty substances is most likely. Recently, a newer technique was developed to perform a balloon dilatation procedure at the bifurcated region by inserting two balloons of different sizes sequentially into a first vessel and a second bifurcated vessel, respectively. However, the procedure of double-balloon sequential dilatations is not very successful in treating the stenosis. When a first vessel is dilated by a first balloon, the inner vessel wall of the first vessel at the bifurcation region tends to temporarily recede because of the balloon's pushing. Once the first balloon is deflated, the inner vessel wall of that first vessel at the bifurcation region bounces back and the dilatation effectiveness is compromised.

The bifurcated balloon is also useful to deploy a bifurcated stent at the bifurcated region of the blood vessels as a further treatment to the stenotic tissues. When a clogged artery is widened, the plaque is broken up and the underlying collagen or damaged endothelium is exposed to the blood flow. Collagen has a pro-thrombotic property, which is a part of the body healing process. Unless the collagen or the damaged endothelium is passivated or modulated, the chance for blood vessel clotting as well as restenosis still exists. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessel walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after a stent is deployed in a body lumen.

Therefore there exists a need in the art for a vascular dilatation catheter to have a bifurcated balloon to inflate the bifurcated region of the two vessels simultaneously. By performing a procedure using a dilatation catheter having a bifurcated balloon, the stenotic region at the bifurcation zone can be effectively treated.

SUMMARY OF THE INVENTION

In general, it is an object of the present invention to provide a bifurcated balloon catheter, such as performing balloon dilatation procedures in a body lumen. It is another object of the present invention to provide a balloon catheter having a bifurcated balloon. The "bifurcated balloon" in this invention is referred to as a balloon having a proximal end and a two-head distal section with two distal ends. In an alternate embodiment, the "bifurcated balloon" in this invention is also referred to as a balloon having two axially oriented compartments, each compartment has a proximal end and a distal end, wherein a portion of the two compartments near their distal ends is separated and a portion of the two compartments near their proximal ends is joined and stuck together. The joining of the two compartments can be achieved by use of glues, epoxy, adhesives, or thermal fusion. The two compartments are not communicable.

It is another object of the present invention to provide a bifurcated balloon over a wire means, wherein the wire means has a proximal end and a two-head distal section with two distal ends. In an alternate embodiment, the wire means comprises two wires, each wire having its own distal end, and its own proximal end, wherein each wire is independently controlled. In one embodiment, the bifurcated balloon catheter is inserted into a body lumen through a pair of guidewires, wherein each guidewire is steerable so that both distal ends are either deflected in the same direction or in two separate directions at the bifurcation region. It is still another object of this invention to provide a method and a stented bifurcated balloon catheter for treating atherosclerotic tissues at the bifurcated region of vascular vessels by deploying the bifurcated stent in place.

The bifurcated balloon generally includes two broad classes. One class is considered noncompliant balloon, formed from a generally nondistensible material such as polyethylene, polyethylene terephthalate, polypropylene, cross-linked polyethylene, polyimide, and the like. The other class is considered compliant balloon, formed from a generally complaint material such as nylon, silicon, latex, polyurethane and the like.

It is a further object of the present invention to provide RF current to the deployed bifurcated stent to treat the stenotic tissue at the bifurcated region. Briefly, heat is generated by supplying a suitable energy source to a metallic stent in contact with the body tissues. A suitable energy source may consist of radiofrequency energy, microwave energy, ultrasonic energy, alternating current energy, or laser energy. The energy can be applied to the bifurcated stent and subsequently to the underlying cellular tissues through the stent. A DIP (dispersive indifferent pad) type pad or electrode that contacts the patient, is connected to the Indifferent Electrode Connector on a RF current generator. Therefore, the RF current delivery becomes effective when a close circuit from a RF generator through a patient and returning to the RF generator is formed. Heat is controlled by the power of the RF current delivered and by the delivery duration. The standard RF current generator means and its applications through a metallic stent means, to a patient are well known for those who are skilled in the art.

It is another object of the present invention to provide a rapid exchange bifurcated balloon catheter for the body lumen. Said catheter comprises a catheter shaft defining an inflation lumen, the inflation lumen having a proximal end and a distal end; an inflatable bifurcated balloon having a proximal end and two distal ends; a wire guide shaft defining a wire guide lumen and having a wire guide means, the wire guide means having a plurality of wire guides, each having a proximal end and a distal end; and two catheter tips, each having a proximal end and a distal end; wherein the distal end of the inflation lumen opens into and is in fluid communication with an interior of the inflatable bifurcated balloon, each of the distal ends of the inflatable bifurcated balloon is sealed by each proximal end of the catheter tips, said coupling being completely distal of the distal end of the inflatable balloon.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of a bifurcated balloon catheter system, comprising a bifurcated balloon, a deployable stent, and/or a RF current generator.

Figure 1:
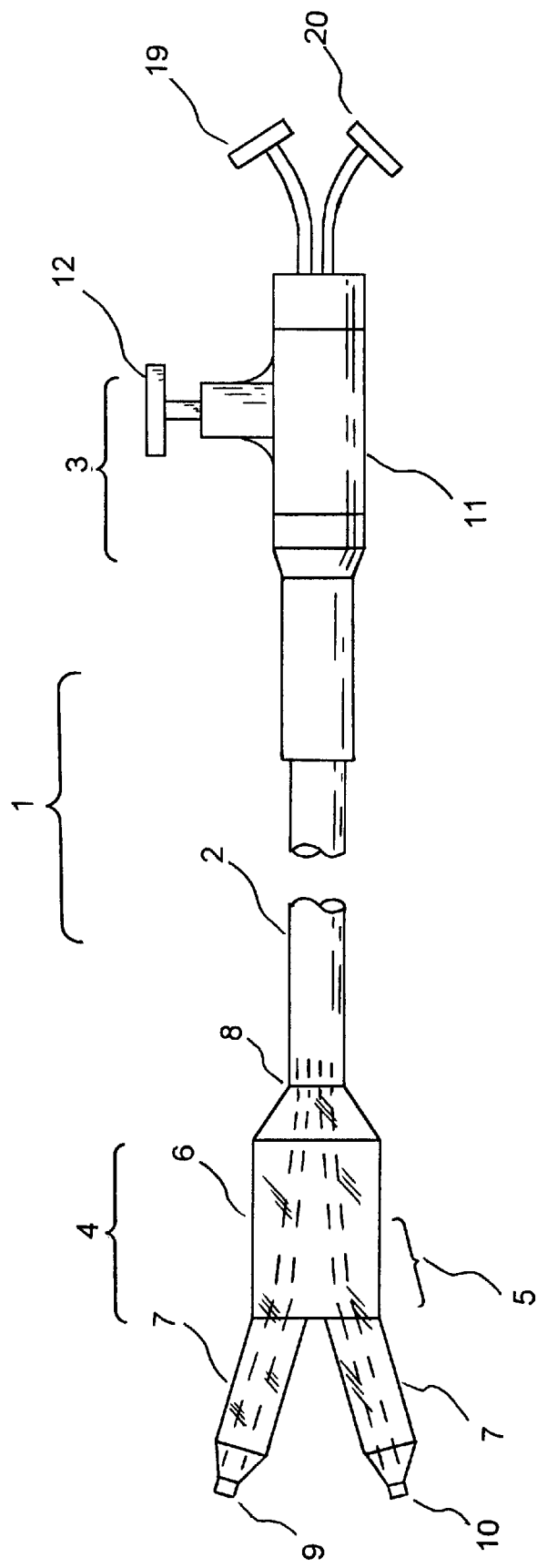
FIG. 1 is a schematic view of a preferred embodiment of a bifurcated balloon catheter of one aspect of the present invention.

FIG. 1 shows a schematic view of a preferred embodiment of a bifurcated balloon catheter 1 of one aspect of the present invention. A catheter comprising additional features known in the vascular dilatation art, such as implantable stents, drug delivery, perfusion and dilatation features, or any combination of these features, can be incorporated into the bifurcated balloon of the present invention as will be readily apparent to one who is skilled in the art. A bifurcated balloon catheter generally comprises an elongate flexible tubular body 2 extending between a proximal control end 3 and a distal functional end 4. The tubular body 2 may be produced in accordance with any known technique for manufacturing a balloon-tipped catheter body, such as by extrusion of a plastic material. In another embodiment, a portion or all of the length of tubular body 2 may comprise a spring coil, solid walled hypodermic needle tubing, braided reinforced wall tubing, or the like. The tubular body 2 is provided with a generally circular cross-sectional configuration having an external diameter in the range from about 0.06 cm to about 0.18 cm. The length is typically in the range of 100 cm to 150 cm. In another embodiment, generally triangular, oval or double-circular cross-sectional configurations can also be used, as well as other noncircular configurations depending upon the intended use.

Tubular body 2 must have sufficient structural integrity to permit the catheter to be advanced to distal arterial locations without buckling or undesirable bending of the tubular body. The tubular body may also need the ability to transmit torque and be flexible for passing through a bifurcated vascular vessel.

As illustrated in FIG. 1, the distal functional end 4 is provided with an inflatable bifurcated balloon 5 having a proximal segment 6 and a distal segment 7, wherein the proximal segment 6 has a proximal end 8 and the distal segment 7 has two distal ends 9 and 10. The proximal control end 3 of catheter 1 is provided with a manifold 11 having a plurality of access ports, as is known in the art. The manifold 11 is provided with two guidewire ports 19 and 20 in an over the wire embodiment and a balloon inflation port 12. A pair of guidewires through guidewire ports 19, 20 may be needed to independently guide the distal ends 9, 10 into their separate vessels at a bifurcated region, if so desired. The bifurcated balloon 5 can also be mounted on a rapid exchange type catheter, in which the proximal guidewire ports 19 and 20 would be unnecessary as is understood in the art. In a rapid exchange embodiment, the proximal guidewire access ports are positioned along the length of the tubular body 2 near the distal functional end 4 of catheter 1.

Figure 2:
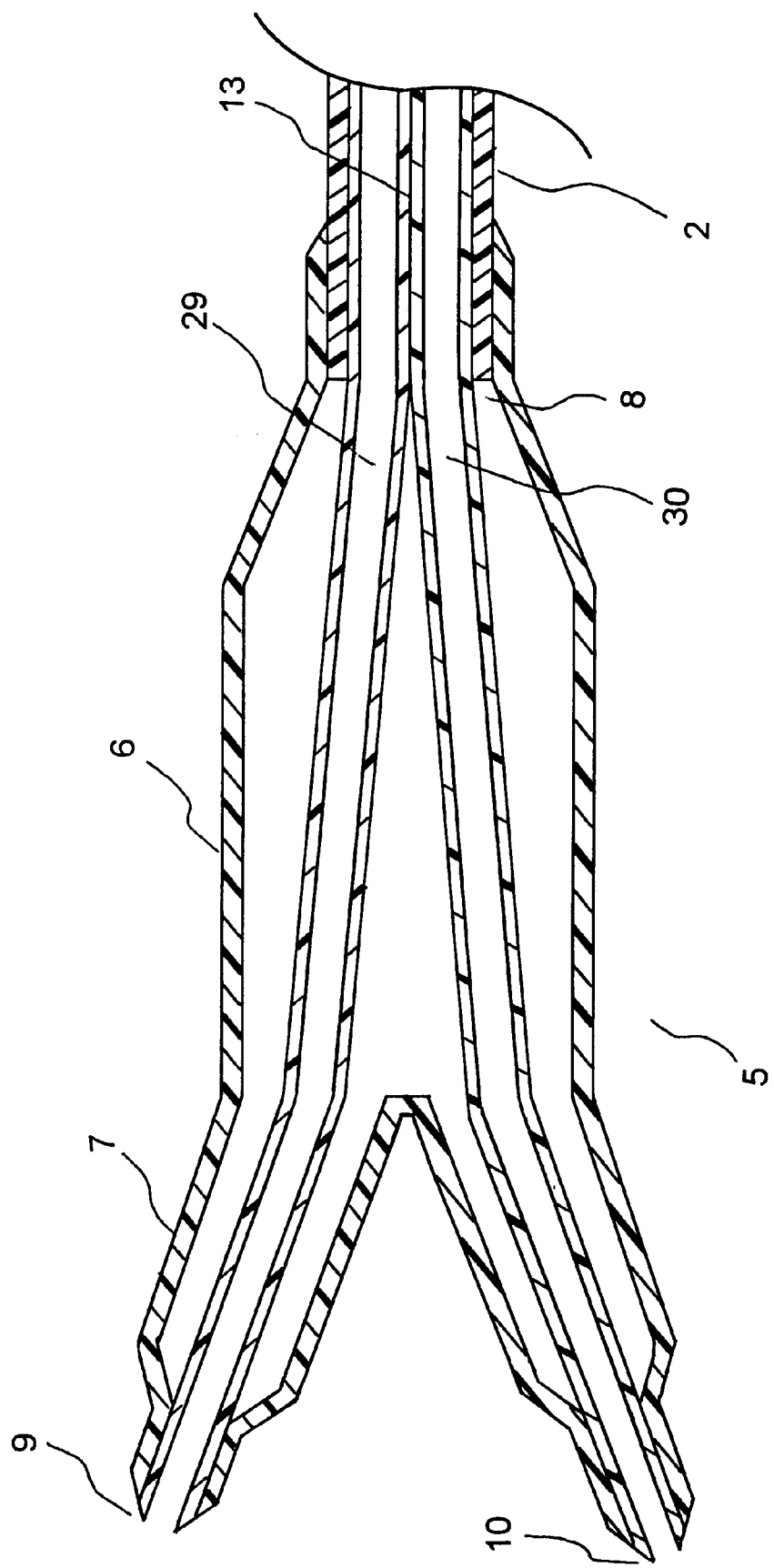
FIG. 2 is a partial cross-sectional view of a preferred embodiment of a bifurcated balloon catheter of one aspect of the present invention.

Referring to FIG. 2, a partial cross-sectional view of a preferred embodiment of a bifurcated balloon catheter 1 of the present invention is illustrated. Preferably, the tubular body 2 is provided with a plurality of guidewire lumens 29, 30 extending all the way through the proximal segment 6 and the distal segment 7 of the balloon 5. The tubular body is also provided with an inflation lumen 13 extending into the proximal end 8 of the balloon 5, wherein the inflation lumen 13 is in communication with an interior of the inflatable bifurcated balloon 5, whereby the distal ends 9, 10 of the inflatable balloon 5 are sealed.

Figure 3:
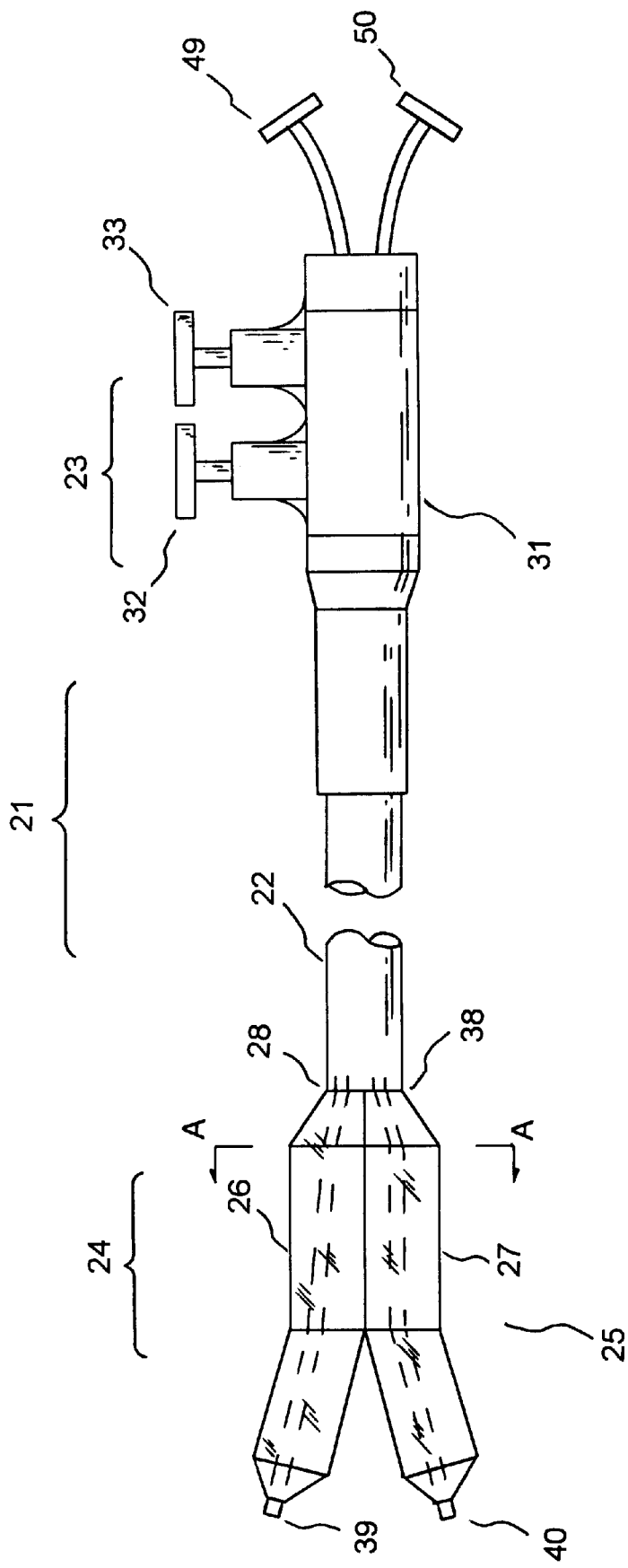
FIG. 3 is a schematic view of a preferred embodiment of a bifurcated balloon catheter of another aspect of the present invention.

FIG. 3 shows a schematic view of a preferred embodiment of a bifurcated balloon catheter 21 of another aspect of the present invention. A bifurcated balloon catheter 21 generally comprises an elongate flexible tubular body 22 extending between a proximal control end 23 and a distal functional end 24. The bifurcated balloon 25 comprises two axially oriented compartments 26 and 27, each compartment having a proximal end 28 or 38 and a distal end 39 or 40, wherein a portion of the two compartments 26, 27 near their distal ends 39, 40 is separated and a portion of the two compartments near their proximal ends 28, 38 is joined together onto the tubular body 22. The proximal control end 23 of catheter 21 is provided with a manifold 31 having a plurality of access ports, as is known in the art. The manifold 31 is provided with two guidewire ports 49 and 50 in an over the wire embodiment and two balloon inflation ports 32 and 33 for the two compartments 26 and 27 of the bifurcated balloon 25. A conventional inflation fluid to inflate a balloon is known to one who is skilled in the art.

Figure 4:
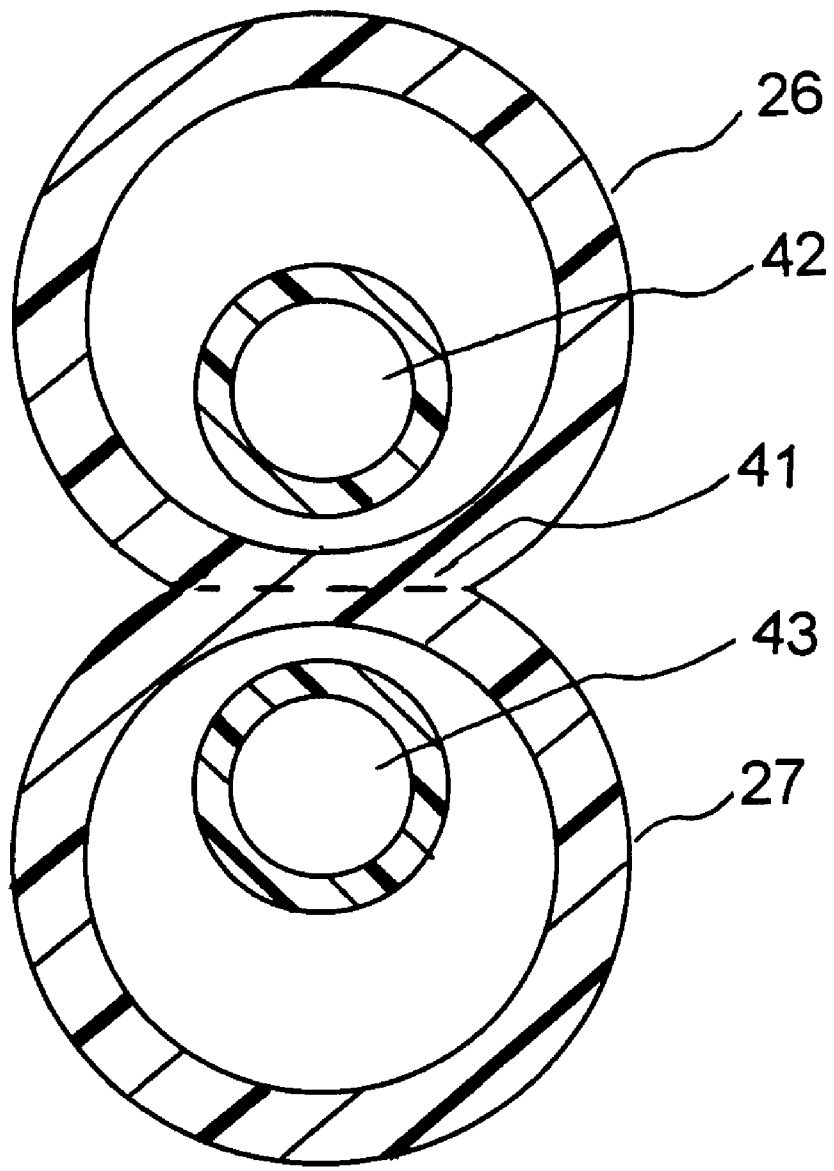
FIG. 4 is a cross-sectional view of another aspect of the present invention from section AA of FIG. 3.

FIG. 4 shows a cross-sectional view of the section A—A of FIG. 3. A portion of the two compartments 26 and 27 is joined together at line 41. The technique for joining two balloons may include use of adhesives or plastic thermal fusion. The bifurcated balloon 25 is also provided with two guidewire lumens 42 and 43, which are connected to the guidewire ports 49 and 50, respectively.

Figure 5:
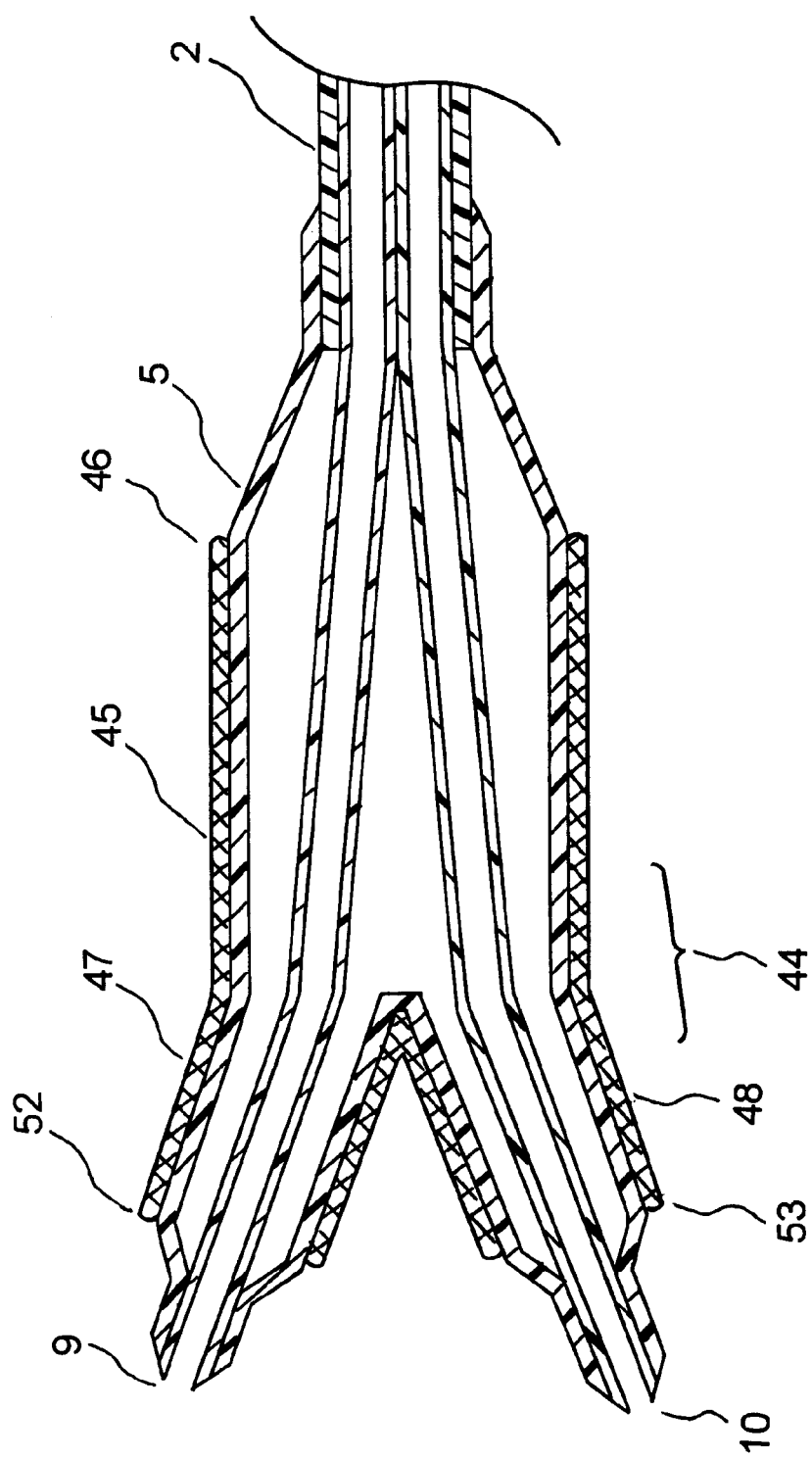
FIG. 5 is a partial cross-sectional view of a preferred embodiment of a bifurcated balloon catheter having a bifurcated stent of one aspect of the present invention.

FIG. 5 shows a partial cross-sectional view of a preferred embodiment of a bifurcated balloon catheter having a bifurcated stent 44 wrapped around and onto a bifurcated balloon 5. The bifurcated stent 44 has a proximal segment 45 with a proximal end 46 and two distal segments 47, 48 with two distal ends 52 and 53. In a particular embodiment, the material for the bifurcated stent of this invention consists of conductive metals such as platinum, iridium, gold, silver, stainless steel, Nitinol, or an alloy of these metals.

Figure 6:
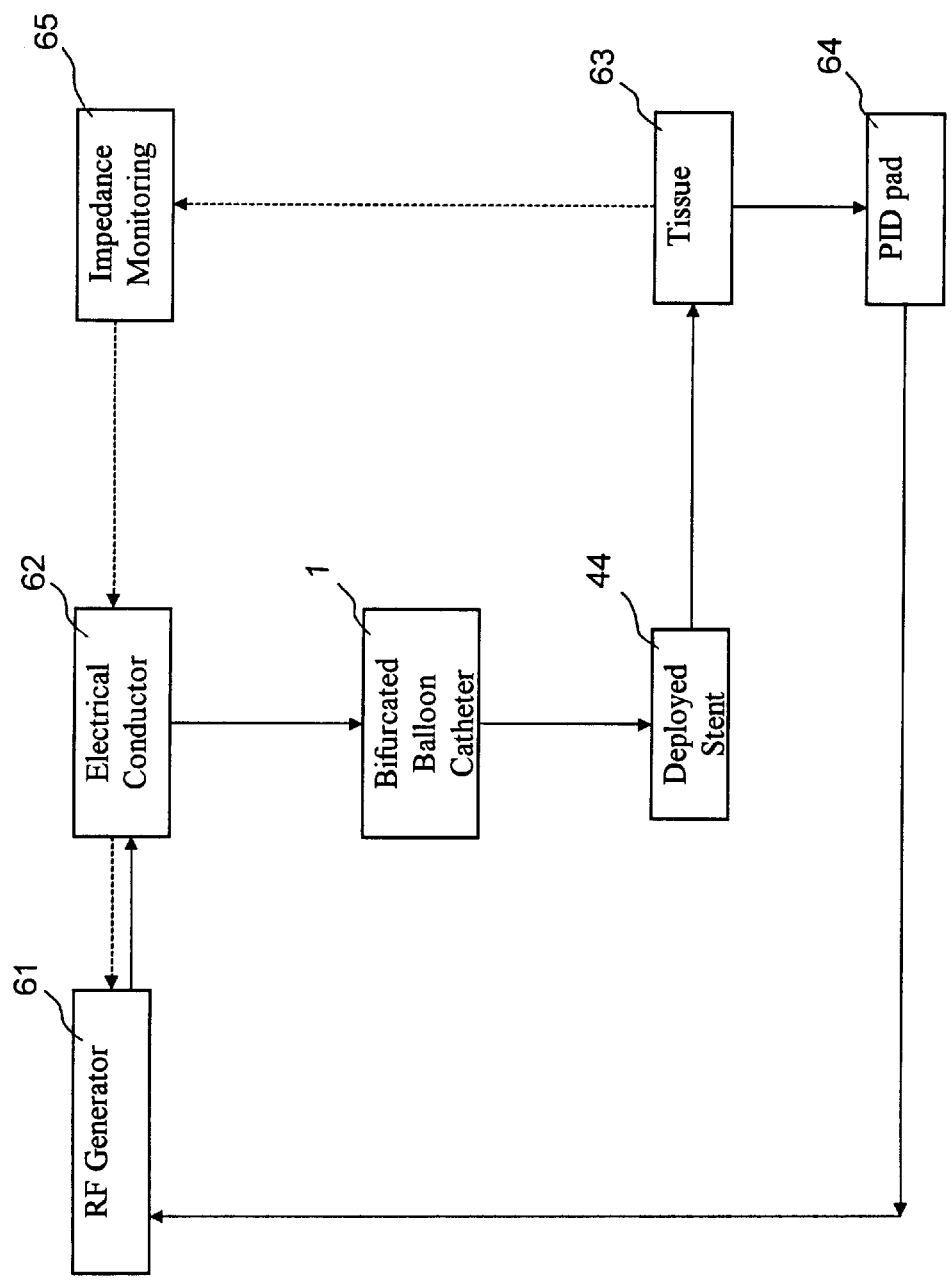
FIG. 6 is a schematic diagram of a RF treatment method in relation to the tissue through a deployed stent from a bifurcated balloon catheter of the present invention.

FIG. 6 shows a schematic diagram of a RF treatment method in relation to a bifurcated tissue through a deployed stent in a patient. A RF current generator 61 is connected to a bifurcated balloon catheter 1 through an electrical conductor 62. A deployed stent 44 of the catheter 1 is to contact the tissue 63 of a patient when the stent 44 is deployed. The metallic bifurcated stent 44 is in close contact with the underlying tissue 63. A DIP (dispersive indifferent pad) type pad 64 that contacts a patient is connected to the Indifferent Electrode Connector on the RF generator 61. Therefore, the RF current delivery becomes effective when a close circuit from a RF generator through a patient and returning to the RF generator is formed. Impedance 65 measured from the tissue contact is to ensure good tissue contact for heat treatment, otherwise the RF current is cutoff when the impedance is unreasonably high. The radiofrequency energy current in this invention is preferably within the range of 50 to 2,000 kHz.

In one particular method of manufacturing a bifurcated balloon for illustration purposes, two low-density polyethylene extrusion stock tubes are used. A first stock tube having an inside diameter of about 0.12 cm and an outside diameter of about 0.16 is used for the proximal segment; while a second stock tube having an inside diameter of about 0.04 cm and an outer diameter of about 0.06 cm is used for the distal segment of a bifurcated balloon. A bifurcated mandrill with a predetermined proximal stem diameter and two distal stem diameters is used to fuse the stock tubes into a bifurcated tube. An appropriate length of a first stock tube is placed onto the proximal stem of said bifurcated mandrill while the two second stock tubes are placed onto the distal stems of said bifurcated mandrill.

The distal end of the first stock tube overlaps and is pressed circumferentially against the proximal ends of the second stock tubes. Appropriate heat is applied to the overlapped region to fuse the stock tubes into a bifurcated tube. A portion of the bifurcated tube is then placed into a mold, which has the shape and dimensions of the desired size of the inflated balloon 5. The bifurcated tube inside the mold is then heated and the interior of the tube is pressurized such that the portion of the tube within the mold expands to the interior dimensions of the mold. The mold is then removed and the balloon 5 is ready to be mounted onto the catheter tubular body 2. In a particular embodiment, before it is placed in a mold for heat blowing, the bifurcated tube may be cross-linked by exposure to an electron beam in accordance with techniques well known in the art.

The balloon is then attached to the tubular body 2 by any of a variety of bonding techniques known to one who is skilled in the art such as solvent bonding or thermal adhesive bonding.

A bifurcated balloon catheter made in accordance with the foregoing designs has been found to benefit certain conventional percutaneous transluminal coronary angioplasty procedures. A method of treating a site in a body lumen using a balloon catheter is illustrated below. The balloon catheter has an elongate, flexible, tubular body. And an inflatable bifurcated balloon is mounted on the tubular body, wherein the bifurcated balloon has a proximal segment and a distal segment. The proximal segment has a proximal end and the distal segment has two distal ends. The method comprises the steps of positioning the catheter within a body lumen so that the bifurcated balloon is adjacent to a treatment site; and inflating the bifurcated balloon to treat the site.

An alternate method of deploying a tubular stent to treat a site within a body lumen using a bifurcated balloon catheter system is illustrated. The balloon catheter has an elongate, flexible, tubular body. And an inflatable bifurcated balloon is mounted on the tubular body, wherein the bifurcated balloon has a proximal segment and a distal segment. The proximal segment has a proximal end and the distal segment has two distal ends. A deployable stent is wrapped around and onto the balloon. The balloon catheter system also comprises a RF current generator, wherein RF current is delivered to the stent. The alternate method comprises the steps of positioning an expandable tubular stent on the bifurcated balloon; positioning the catheter within a body lumen adjacent a treatment site; inflating the bifurcated balloon to expand the tubular stent, and optionally delivering RF current through an electrical conductor to the tubular stent to treat the site.

After the stenosis at the bifurcated region is compressed to or beyond the native diameter of the vessel, or after the stent is deployed, or optionally after RF therapy is applied to the stent, the balloon is deflated and the catheter withdrawn. In accordance with the method of deploying and/or implanting a tubular stent, an expandable stent is positioned about the deflated balloon of a bifurcated balloon catheter. The balloon is thereafter inflated to a desired diameter and the expanded tubular stent is left in place after the balloon is deflated.

From the foregoing description, it should now be appreciated that an inflatable bifurcated balloon catheter for treating the bifurcated region of blood vessels has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method of deploying a tubular stent to treat a site within a body lumen using a bifurcated balloon, comprising the steps of:

providing a catheter of the type having an elongate, flexible, tubular body; and an inflatable bifurcated balloon on the tubular body, wherein the bifurcated balloon has a proximal segment and a distal segment, and wherein the proximal segment has a proximal end and the distal segment has two distal ends;

positioning an expandable tubular stent on the bifurcated balloon;

positioning the catheter within a body lumen adjacent a treatment site;

inflating the bifurcated balloon to expand the tubular stent; and providing a RF current generator, wherein a RF current is delivered through an electrical conductor to the tubular stent to treat the site.

* * * * *